United States Patent [19]

Molloy et al.

[11] Patent Number: 5,468,620
[45] Date of Patent: Nov. 21, 1995

[54] METHODS AND DEVICE FOR GLYCOSYLATION ANALYSIS

[75] Inventors: James O. Molloy, Belmont; Denise V. Pollard-Knight, St. Albans, both of United Kingdom

[73] Assignee: Fisons PLC, Suffolk, England

[21] Appl. No.: 104,077

[22] PCT Filed: Mar. 9, 1992

[86] PCT No.: PCT/GB92/00414

§ 371 Date: Nov. 29, 1993

§ 102(e) Date: Nov. 29, 1993

[87] PCT Pub. No.: WO92/15706

PCT Pub. Date: Sep. 17, 1992

[30] Foreign Application Priority Data

Mar. 9, 1991 [GB] United Kingdom ............ 9105043
Jul. 19, 1991 [GB] United Kingdom ............ 9115608

[51] Int. Cl.[6] ............................ C12Q 1/34; C12M 1/40; G01N 33/53
[52] U.S. Cl. .......................... 435/7.1; 435/14; 435/18; 435/176; 435/808; 435/817; 435/287.1; 435/287.2; 435/288.7; 436/94; 436/524; 436/531; 436/807; 422/82.08; 422/82; 422/11; 356/352; 204/403
[58] Field of Search ................... 435/4, 7.1, 14, 435/18, 96, 174, 176, 291, 288, 808, 817, 961; 436/94, 524, 531, 805, 807; 422/57–58, 82.06–82.09, 82.11; 204/403, 153.12; 356/352; 427/2

[56] References Cited

U.S. PATENT DOCUMENTS

| | | | |
|---|---|---|---|
| 4,857,273 | 8/1989 | Stewart | 422/68 |
| 4,865,995 | 9/1989 | Dairaku | 436/94 |
| 5,081,037 | 1/1992 | Kariyone et al. | 435/288 |
| 5,183,743 | 2/1993 | Corey | 435/18 |
| 5,192,415 | 3/1993 | Yoshioka et al. | 204/403 |
| 5,192,666 | 3/1993 | Ikenaka et al. | 435/22 |
| 5,229,833 | 7/1993 | Stewart | 356/364 |
| 5,246,846 | 9/1993 | Pittner et al. | 435/174 |

FOREIGN PATENT DOCUMENTS

| | | |
|---|---|---|
| 0127438 | 12/1984 | European Pat. Off. . |
| 8402578 | 5/1984 | WIPO ............ 435/973 |
| WO90/11510 | 6/1990 | WIPO . |
| WO90/11510 | 10/1990 | WIPO . |

OTHER PUBLICATIONS

*Chemical Abstracts*, vol. 79, No. 7, 1973, p. 119 Abstract #39596.

*Chemical Abstracts*, vol. 113, No. 19, 1990. Abstract #168390.

Primary Examiner—Carol A. Spiegel
Attorney, Agent, or Firm—Marshall, O'Toole, Gerstein, Murray & Borun

[57] ABSTRACT

Methods of glycosylation analysis are described in which a sample containing one or more specific oligosaccharide(s) (the analyte) is contacted with a surface on which is immobilized a glycosidase specific for the analyte and/or a specific binding partner for a product of the action of a glycosidase on the analyte. The surface may be the active surface of a biosensor, e.g., a biosensor based on the principle of frustrated total reflection.

8 Claims, 2 Drawing Sheets

METHODS AND DEVICE FOR GLYCOSYLATION ANALYSIS

This invention relates to apparatus and methods for the determination of biomolecules in samples of biological origin, in particular for the characterisation of oligosaccharides on glycoproteins and glycohormones.

BACKGROUND OF THE INVENTION

The ubiquitous distribution of glycoconjugates at cell surfaces, extracellular matrices and within particular organelles has focused a great deal of research on the study of glycoconjugates as molecular determinants in cellular function, intracellular processing and intracellular interactions. Oligosaccharides may be covalently linked to the protein through an asparagine side chain (N-linked) or through a serine or threonine side chain (O-linked).

Differential glycosylation of a polypeptide can create different subsets of glycoproteins which may have different physical and biochemical properties [Rademacher, T. W., Parekh, R. B., and Dwek, R. A. (1988) Annual Review Biochemistry 57, 785–838]. This may result in functional diversity leading to different disease states. For example, there is a shift in the population of the glycosylated forms of IgG towards those with a higher content of agalactosyl biantennary N-linked oligosaccharides in active rheumatoid arthritis, tuberculosis and Crohn's disease. This shift is thought to be involved in disease pathogenesis [Parekh, R. B., Dwek, R. A., Sutton, B. J. et al (1985) Nature 316, 452–457].

One known method of analysis of glycoproteins involves the following steps:

i) controlled hydrazinolysis of the glycoprotein to release intact oligosaccharide moieties or digestion with a glycopeptidase, ii) labelling with tritium in a reduction reaction, iii) digestion of the oligosaccharides with specific glycosidases, and iv) fractionation of the resulting products by chromatography.

The fractionation profile is compared to the elution parameters of standard oligosaccharide moieties to give a compositional analysis. The oligosaccharide moieties may also be released from the glycoprotein using enzymes such as endoglycosidase H.

An alternative strategy based on fast atom bombardment mass spectroscopy for analysis of glycoproteins has also been developed [Dell, A., Advances in Carbohydrate Chemistry and Biochemistry 45, 19–72].

These methods are time-consuming, and involve the use of radioactivity and/or sophisticated equipment.

We have now devised methods and apparatus for glycosylation analysis which overcome or substantially mitigate certain of the above-mentioned disadvantages, and are particularly useful when very detailed analysis of oligosaccharide composition is not required.

SUMMARY OF THE INVENTION

According to the invention there is provided a method of determining one or more specific oligosaccharide(s) (the analyte) in a sample, which method comprises contacting the sample with a surface on which is immobilised a glycosidase specific for the analyte.

In a first variant of the method according to the invention, there is added, simultaneously with the sample, a substrate for the glycosidase. The substrate is labelled in such a way that it is converted by the glycosidase to a detectable product. The labelled substrate competes with the analyte for binding to the glycosidase, such that the concentration of labelled product is inversely proportional to the concentration of analyte present in the sample.

The types of labels which may be used include substrates that result in a fluorescent, absorbent or luminescent product. For example, many glycosides are available as 4-nitrophenyl-glycosides. The reaction of these with their specific glycosidases results in the release of 4-nitrophenol, a yellow product which absorbs at 405 nm. Many substrates may also be labelled with the fluorogenic group methylumbelliferone which is non-fluorogenic when incorporated into the substrate and fluorogenic when the group is released on reaction with an enzyme. Alternatively, reaction of the substrate with the enzyme may result in the formation of an insoluble product, thereby increasing the refractive index in the vicinity of the surface. This may be detected when the surface is the surface of an optical biosensor. It may also be possible to detect the enzyme reaction directly by electrochemical means.

Several glycosidases specific for different saccharide moieties may be immobilised on the surface, eg in discrete regions, allowing analysis for several types of saccharide moieties simultaneously in a single sample.

In a second variant of the method according to the invention, the products of the reaction of the analyte with the glycosidase are bound by immobilised specific binding partners, eg antibodies or lectins. Labelled saccharide moieties otherwise identical to those to be detected are added before, after or simultaneously with the sample. The products of reaction between the analyte and the enzyme then compete with the labelled saccharides for binding to the immobilised specific binding partners. If the labelled saccharides have been pre-complexed with the specific binding partners, then they may be displaced by the reaction products.

The labelled saccharides may, like the labelled products in the first variant of the method, be fluorogenic, absorbent or may have a high refractive index. Again, the concentration of labelled species in the vicinity of the surface is inversely proportional to the concentration of analyte in the sample.

Specific binding partners for different products of the glycosidase reaction may be immobilised in a specific pattern on the surface, enabling a number of products to be determined simultaneously.

The methods according to the invention are advantageous in that they are simple to perform, allow several analyses on a single sample and are relatively cheap. They also avoid the need for detailed analyses on all samples. The glycoproteins may be further analysed by known methods if necessary.

Some of the glycosidases which may be immobilised on the surface are given in the 'Materials and Methods' section of Parekh et al (1987), The EMBO Journal 6, 1233–1244. Details can be found in Kobata, A. (1979), Analytical Biochemistry, 100, 1–14, and Kobata, A. (1984) in Biology of Carbohydrates (Eds Ginsburg, V. & Robbins, P. W.) John Wiley and Sons, New York, Vol. 2, Chap. 2, pp 87–162.

Both N- and O-glycosylation patterns and the occurrence of oligomannose structures, core $\alpha$ (1,6)-linked fucose residues, hybrid oligosaccharides, complex oligosaccharides, polylactosaminoglycan structures and terminal gal→ may be analysed using the methods. The other information which may be provided by the analysis is detailed in Dell et al (1988), Biochemie 70, 1435–1444.

The methods may be used in a differential analysis or mode. For example, for the diagnosis of diseases with an arthritic component such as rheumatoid arthritis, the deficiency of galactose in a sample of patient's blood serum or synovial fluid, or an Ig component or fragment is compared with that of a normal patient or standard. In patients with rheumatoid arthritis the serum IgG has an increased number of oligosaccharide moieties whose outer arms lack galactose and terminate in N-acetylglucosamine. This change in glycosylation is generally measured by releasing the oligosaccharides from the IgG with hydrazine followed by digestion of the oligosaccharides with exoglycosidases of defined specificities.

In a further alternative method according to the invention, the glycosidase reaction is performed on the sample remote from the surface. The reaction products are then analysed on the surface using immobilised lectins and/or antibodies which are immobilised in a specific pattern. Examples of antibodies which may be used are described in Thall, A. and Galili, U. (1990) Biochemistry 29, 3959–3965, and Christopher, J. E., Caterson, B. and Baker, J. R. (1980) J. Biological Chemistry 255, 7102–7105.

The biomolecules (enzymes and, where used, antibodies or lectins) immobilised on the surface may be covalently bound to the surface by methods which are well known to those skilled in the art. In general, however, in order to facilitate immobilisation, the surface will be derivatised or activated. The derivatisation or activation of the surface will be such as to provide coupling sites for the species to be immobilised without appreciably affecting the reactivity or affinity of the immobilised species for the analyte or reaction product. Examples of lectins which may be used are described in Lis, H. and Sharon, N. (1986) Ann. Rev. Biochem. 55, 35–67.

For example, the surface may be reacted with a silane-based coupling compound in a known manner. A suitable such reagent is, for example, a terminal amino-alkyl trimethoxysilane, eg the 3-aminopropyl compound, used at a concentration of about 2% w/v in acetone. Details of immobilisation techniques using this reagent have been described by Weetall [see, for example, U.S. Pat. No. 3,652,761 and "Immobilised Biochemicals and Affinity Chromatography", R. B. Dunlop (Ed), Plenum Press, New York (1974), pp191–212], along with a description of other silyl compounds and the methods by which carboxyl, amino and other reactive groups may be covalently bound to various inorganic materials.

After reaction with the amino-silane reagent, the amino terminals immobilised on the surface may in turn be reacted with glutaraldehyde (eg a 2% solution of pH 7), excess reagents removed, and the activated surface with immobilised aldehyde groups then treated with a solution of the species to be immobilised.

An alternative method for coupling biomolecules to a dielectric surface involves treatment with epoxy-silane reagents, especially glycidyloxypropyltrimethoxysilane, eg at a concentration of about 2% v/v in toluene for about 2 hours at 70° C. as described by Herman et al [J Chromatogr Sci (1981), 19(9), 470–476]. In this method the use of aldehyde reagents is unnecessary, since the epoxysilylated surface can react directly with the species to be immobilised.

Methods of immobilising species to polymeric or metallic surfaces are also well-known, and those skilled in the art will recognise the applicability of these methods when the surface is polymeric or metallic. For example, the coupling may be in the form of the substitution of an appropriate radical for a hydrogen on any of a polymer's functional groups.

It is also possible for the biomolecules to be immobilised on the surface via an intermediate layer of, for example, gel or other particles.

The surface may be a solid surface as used in conventional solid phase assays, eg ELISA. However, it is found particularly convenient to use as the surface the active surface of a biosensor. The types of sensor which may be used include electrochemical, surface acoustic wave, and surface plasmon resonance devices, and sensors which can be used to detect fluorescence, eg those based on total internal reflection.

Examples of known forms of biosensor are described in European Patent No. 0075353, PCT Patent Application No. WO 90/06503, British Patent No. 2174802 and European Patent Application No. 0305109.

The use of biosensors for glycosylation analysis is believed to be novel, and according to a further aspect of the invention, there is provided a method of glycosylation analysis which comprises contacting a sample containing an oligosaccharide analyte with the surface of a biosensor upon which is immobilised a glycosidase specific to the analyte, or contacting a sample containing a product of a glycosidase reaction of such an analyte with the surface of a biosensor upon which is immobilised a specific binding partner for that product.

According to a related aspect of the invention, there is provided a biosensor having an active surface upon which is immobilised a glycosidase specific to an oligosaccharide analyte, or a specific binding partner for a product of a glycosidase reaction of such an analyte.

A preferred form of biosensor is one based on the principle of frustrated total reflection (FTR). The principles of FTR are well-known; the technique is described, for example, by Bosacchi and Oehrle [Applied Optics (1982), 21, 2167–2173]. An FTR device for use in immunoassay is disclosed in U.S. Pat. No. 4,857,273 and comprises a cavity layer bounded on one side by the sample under investigation and on the other side by a spacer layer which in turn is mounted on a substrate. The substrate-spacer layer interface is irradiated with monochromatic radiation such that total reflection occurs, the associated evanescent field penetrating through the spacer layer. If the thickness of the spacer layer is correct and the incident parallel wave vector matches one of the resonant mode propagation constants, the total reflection is frustrated and radiation is coupled into the cavity layer. The cavity layer must be composed of material which has a higher refractive index than the spacer layer and which is transparent at the wavelength of the incident radiation.

More recently, FTR biosensors have been described [see, for example, PCT Patent Applications WO 90/06503 and WO 91/06862] in which the cavity layer is a thin film of relatively high refractive index material, typically an inorganic oxide.

Typically, an FTR biosensor comprises a) a cavity layer of dielectric material of refractive index $n_3$, b) a dielectric substrate of refractive index $n_1$, and c) interposed between the cavity layer and the substrate, a dielectric spacer layer of refractive index $n_2$.

In use, the interface between the substrate and the spacer layer is irradiated with light such that total reflection occurs. In this context, 'light' may include not only visible light but also wavelengths above and below this range, eg in the ultra-violet and infra-red.

Resonant propagation of a guided mode in the cavity layer will occur, for a given wavelength, at a particular angle of incidence of the exciting radiation. Thus, two basic measurement approaches are possible: scanning the angle of incidence at fixed wavelength or scanning the wavelength at a fixed angle of incidence. The former approach, using monochromatic radiation, is preferred since it allows the use of a laser source, simplifying the problem of optical collimation, and avoids dispersion effects, thereby simplifying the analysis of the results.

The angular position of the resonant effect depends on various parameters of the biosensor device, such as the refractive indices and thicknesses of the various layers. In general, it is a pre-requisite that the refractive index $n_3$ of the cavity layer and the refractive index $n_1$ of the substrate should both exceed the refractive index $n_2$ of the spacer layer. Also, since at least one mode must exist in the cavity to achieve resonance, the cavity layer must exceed a certain minimum thickness.

The cavity layer is preferably a thin-film of dielectric material. Suitably transmissive dielectric materials for the cavity layer include zirconium dioxide, titanium dioxide, aluminium oxide and tantalum oxide.

The cavity layer may be prepared by known techniques, eg vacuum evaporation, sputtering, chemical vapour deposition or in-diffusion.

The dielectric spacer layer must also be suitably transmissive to the incident radiation and must have a lower refractive index than both the cavity layer and the substrate. The layer may, for example, comprise an evaporated or sputtered layer of magnesium fluoride. In this case an infra-red light injection laser may be used as light source. The light from such a source typically has a wavelength around 800 nm. Other suitable materials include lithium fluoride and silicon dioxide. Apart from the evaporation and sputtering techniques mentioned above, the spacer layer may be deposited on the substrate by a sol-gel process, or be formed by chemical reaction with the substrate.

The sol-gel process is particularly preferred where the spacer layer is of silicon dioxide.

The refractive index of the substrate ($n_1$) that ($n_2$) of the spacer layer but the thickness of the substrate is generally not critical to the performance of the invention.

By contrast, the thickness of the cavity layer must be so chosen that resonance occurs within an appropriate range of coupling angles. The spacer layer will typically have a thickness of the order of several hundred nanometers, say from about 200 nm to 2000 nm, more preferably 500 to 1500 nm, eg 1000 nm. The cavity layer typically has a thickness of a few tens of nanometers, say 10 to 200 nm, more preferably 30 to 150 nm, eg 100 nm.

It is particularly preferred that the cavity layer has a thickness of 30 to 150 nm and comprises a material selected from zirconium dioxide, titanium dioxide, tantalum oxide and aluminium oxide, and the spacer layer has a thickness of 500 to 1500 nm and comprises a material selected from magnesium fluoride, lithium fluoride and silicon dioxide, the choice of materials being such that the refractive index of the spacer layer is less than that of the cavity layer.

Preferred materials for the cavity layer and the spacer layer are tantalum oxide and silicon dioxide respectively.

Any convenient source of radiation may be used as the source of the incident light but it is preferable to use monochromatic radiation and the most convenient source of such radiation is a laser. The choice of laser will depend inter alia on the materials used for the various layers of which some examples have already been given.

The scanning of angle may be performed either sequentially or simultaneously ie by varying the angle of incidence of a parallel beam of light or by simultaneously irradiating over a range of angles using a fan-shaped beam of light as described (in connection with SPR) in European Patent Application No. 0305109A. In the former case, a single-channel detector may be used which is mechanically scanned over a range of angles; in the latter case, in which a range of angles is irradiated simultaneously, it will generally be necessary to use a multi-channel detector having angular resolution.

At resonance, the incident light is coupled into the cavity layer by FTR, propagates a certain distance along the cavity layer, and couples back out (also by FTR). The propagation distance depends on the various device parameters but is typically of the order of 1 or 2 mm.

In general, at resonance, the reflected light will undergo a phase change and it may be the angular position at which this phase change occurs which is detected.

Changes on the surface of the cavity layer may cause changes in the thickness of the layer of immobilised biochemicals and hence shift the angular position of the resonance. Alternatively or in addition, there may be a reduction in the intensity of the reflected light, eg if the immobilised species are absorbing at the wavelength of the incident radiation, or differences in fluorescent or luminescent intensity.

BRIEF DESCRIPTION OF THE DRAWINGS

The invention will now be described in more detail with reference to the accompanying drawings, in which.

DESCRIPTION OF THE PREFERRED EMBODIMENTS

Figure 1:
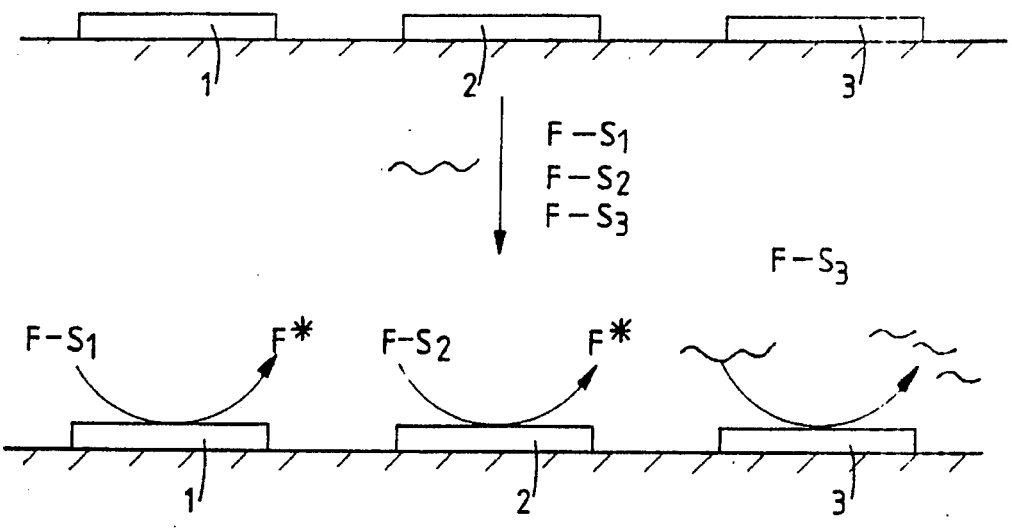
FIG. 1 is a schematic illustration of a first method of glycosylation analysis according to the invention.

Referring first to FIG. 1, a method of glycosylation analysis is carried out using a biosensor, eg an FTR-based resonant optical biosensor, on the surface of which are immobilised several (in the case shown, three) patches of different glycosidases 1,2,3, each of which is specific to a particular saccharide moiety.

A sample containing the oligosaccharide analyte (represented by the wavy line), to which glycosidase 3 is specific, is contacted with the surface of the device, together with labelled substrates F-$S_1$, F-$S_2$, F-$S_3$, which are specific for glycosidases 1,2,3 respectively.

F-$S_1$ and F-$S_2$ are converted by the corresponding glycosidases 1,2 to fluorescent products F*. The analyte present in the sample, however, competes with substrate F-$S_3$ for binding to glycosidase 3, resulting in a reduction in the fluorescent intensity in the vicinity of that glycosidase. This arrangement permits the simultaneous determination of three oligosaccharides. In the case shown, only one is present, as evidenced by the reduced fluorescent intensity at glycosidase 3 compared with the patches of the other glycosidases 1,2.

Figure 2:
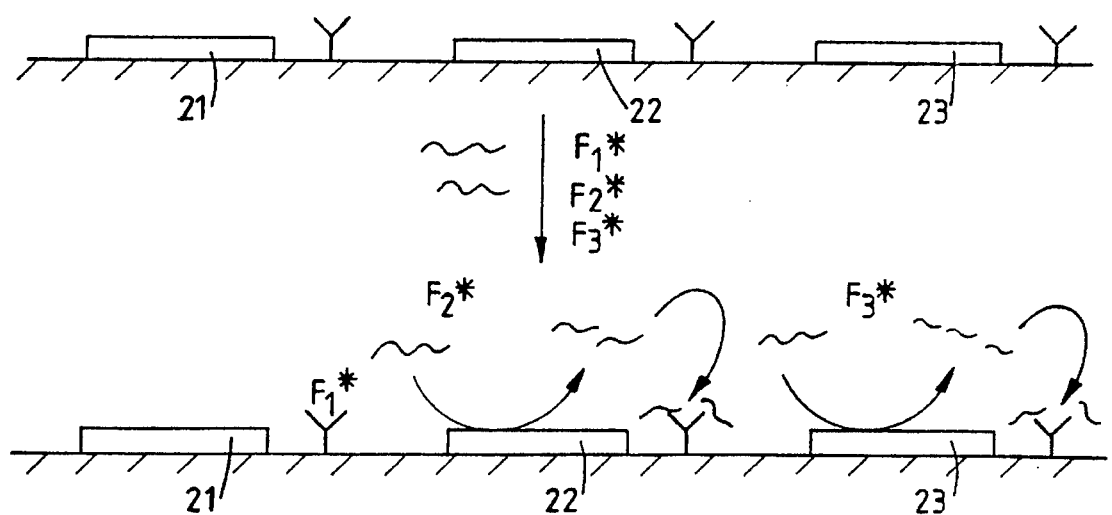
FIG. 2 is a schematic illustration of a second method of glycosylation analysis.

In the method shown in FIG. 2, not only are specific glycosidases 21,22,23 immobilised on the sensor surface but also antibodies specific to the reaction products of those glycosidases. The surface is contacted with a sample containing analyte oligosaccharides and saccharides $F_1^*, F_2^*, F_3^*$ which are labelled but otherwise identical to the products of the action of the glycosidases 21,22,23.

The analyte oligosaccharides are cleaved by the corresponding immobilised glycosidases to give reaction products which compete with fluorescently-labelled saccharides $F_1^*, F_2^*, F_3^*$ for binding to the immobilised antibodies. Once again, therefore, the presence of a particular oligosaccharide in the sample is associated with a reduction in the intensity of fluorescence in the vicinity of the corresponding immobilised antibody.

Figure 3:
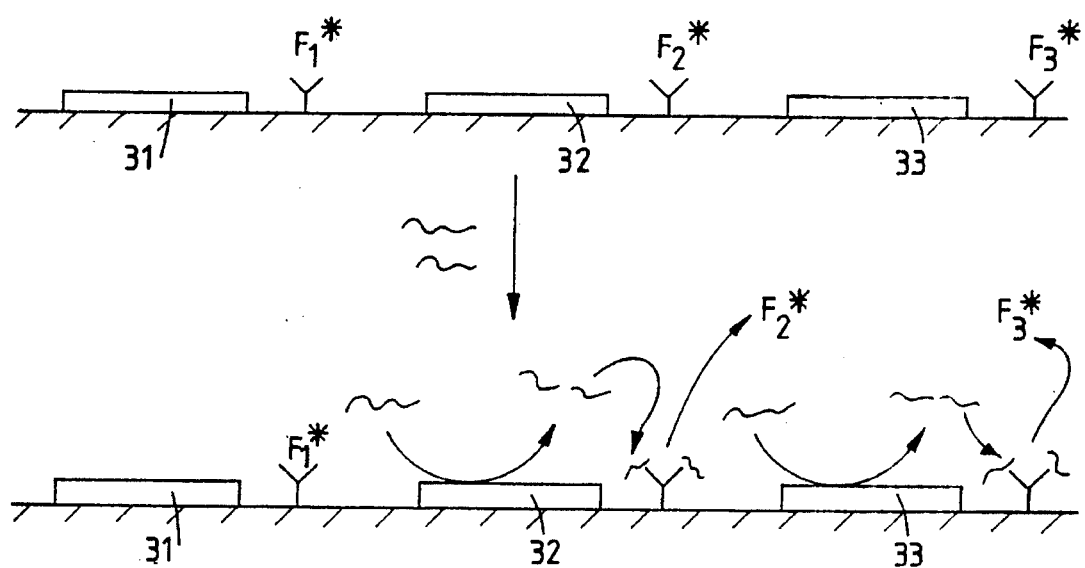
FIG. 3 is a schematic illustration of a third method of glycosylation analysis.

In the variation shown in FIG. 3, again specific glycosidases 31,32,33 are immobilised on the sensor surface together with antibodies specific to the reaction products of those glycosidases. In this case, however, the antibodies are pre-complexed with labelled saccharides $F_1^*, F_2^*, F_3^*$ which are then displaced by the products of the glycosidase reaction, again resulting in localised reduction in fluorescent intensity.

In a further modification, the methods of FIG. 1 and 2 may be performed sequentially and detected by different active patches on the sensor surface.

We claim:

1. A method of assaying a sample for one or more oligosaccharides of a group of preselected analyte oligosaccharides, which method comprises
   (a) providing a biosensor comprising a surface comprising a plurality of discrete spatial sets of adjacent enzymatic and binding regions, wherein the enzymatic region of each set has immobilized thereon a glycosidase which hydrolyzes a preselected one of said analyte oligosaccharides to produce a known saccharide reaction product and the adjacent binding region has immobilized thereon a binding partner which specifically binds to said known saccharide reaction product and to said known saccharide reaction product conjugated to a detectable label:
   (b) providing a labelled reagent comprising each of said known saccharide reaction products conjugated to said detectable label;
   (c) contacting said sample with said biosensor;
   (d) before, after, or simultaneously with step (c), contacting said biosensor with said labelled reagent; and
   (e) measuring the amount of said detectable label bound in each said binding region as an indication of the presence or amount of each of said preselected analyte oligosaccharides in said sample.

2. The method as claimed in claim 1, wherein the labelled reagent is contacted with said biosensor prior to step (c).

3. The method as claimed in claim 1, wherein the detectable label is fluorescent.

4. A method of assaying a sample for one or more oligosaccharides of a group of preselected analyte oligosaccharides, which method comprises
   (a) providing a biosensor comprising a surface comprising a plurality of discrete spatial binding regions, each of which has immobilized thereon antibodies and/or lectins which specifically bind one of a set of known saccharide reaction products prepared by glycosidase hydrolysis of a preselected one of said analyte oligosaccharides;
   (b) providing a reagent comprising a plurality of different glycosidases each of which is specific to one of said analyte oligosaccharides;
   (c) contacting said sample with said reagent to form a sample/reagent mixture containing said known saccharide reaction products;
   (d) contacting said biosensor with said sample/reagent mixture; and
   (e) measuring the amount of said known saccharide reaction products bound in each said binding region as an indication of the present or amount of each of said preselected analyte oligosaccharides in said sample.

5. A biosensor having a surface upon which are immobilized, in discrete spatial regions, a plurality of different specific binding partners for products of glycosidase reactions of oligosaccharide analytes;
   wherein said biosensor is based on frustrated total reflection, and comprises
      (a) a cavity layer of transparent dielectric material of refractive index $n_3$,
      (b) a dielectric base of refractive index $n_1$, and
      (c) interposed between the cavity layer and the base, a dielectric spacer layer of refractive index $n_2$, $n_2$ being less than both $n_1$ and $n_3$.

6. The biosensor as claimed in claim 5, in which the spacer layer has a thickness of from about 200 nm to 2000 nm, and the cavity layer has a thickness of from 10 to 200 nm.

7. The biosensor as claimed in claim 5, in which the cavity layer has a thickness of 30 to 150 nm and comprises a material selected from zirconium dioxide, titanium dioxide, tantalum oxide, and aluminum oxide, and the spacer layer has a thickness of 500 to 1500 nm and comprises a material selected from magnesium fluoride, lithium fluoride, and silicon dioxide, the choice of materials being such that the refractive index of the spacer layer is less than that of the cavity layer.

8. A biosensor having a surface upon which are immobilized, in discrete spatial regions, a plurality of different glycosidases, wherein said biosensor is based on frustrated total reflection, and comprises
   (a) a cavity layer of transparent dielectric material of refractive index $n_3$,
   (b) a dielectric base of refractive index $n_1$, and
   (c) interposed between the cavity layer and the base, a dielectric spacer layer of refractive index $n_2$, $n_2$ being less than both $n_1$ and $n_3$.

* * * * *

UNITED STATES PATENT AND TRADEMARK OFFICE
CERTIFICATE OF CORRECTION

PATENT NO. : 5,468,620
DATED : November 21, 1995
INVENTOR(S) : MOLLOY ET AL.

It is certified that error appears in the above-identified patent and that said Letters Patent is hereby corrected as shown below:

Column 5, line 43, "($n_1$) that" should be --($n_1$) must be greater than that--.

Signed and Sealed this

Twenty-sixth Day of March, 1996

*Attest:*

BRUCE LEHMAN

*Attesting Officer*      *Commissioner of Patents and Trademarks*